United States Patent [19]

Nakamori et al.

[11] 4,224,409

[45] Sep. 23, 1980

[54] METHOD FOR PRODUCING L-PROLINE BY FERMENTATION

[75] Inventors: Shigeru Nakamori, Yokohama; Hajimu Morioka, Kawasaki; Fumihiro Yoshinaga, Fujisawa, all of Japan

[73] Assignee: Ajinomoto Company, Incorporated, Tokyo, Japan

[21] Appl. No.: 7,782

[22] Filed: Jan. 30, 1979

[30] Foreign Application Priority Data

Feb. 1, 1978 [JP] Japan ................................. 53-10660

[51] Int. Cl.$^2$ ........................................... C12P 13/24
[52] U.S. Cl. ................................................. 435/107
[58] Field of Search .................... 195/29, 47; 435/107

[56] References Cited

U.S. PATENT DOCUMENTS 3,819,483  6/1974  Yoshinaga et al. .................... 195/29

Primary Examiner—Lionel M. Shapiro
Attorney, Agent, or Firm—Oblon, Fisher, Spivak, McClelland & Maier

[57] ABSTRACT

A method for producing L-proline by fermentation which comprises culturing an L-proline producing mutant in a culture medium until L-proline is accumulated in the culture medium, and recovering the accumulated L-proline; said mutant belonging to the genus Brevibacterium, Corynebacterium or Microbacterium and being resistant to DL-3,4-dehydroproline.

9 Claims, No Drawings

METHOD FOR PRODUCING L-PROLINE BY FERMENTATION

BACKGROUND OF THE INVENTION

1. Field of the Invention

This invention relates to a method for producing L-proline by fermentation.

2. Description of the Prior Art

Hitherto, an isoleucine or arginine requiring mutant of the genus Brevibacterium or Corynebacterium (Japanese Published Examined Patent Application No. 11751/1968), an isoleucine requiring and sulfaguanidine resistant mutant of the genus Brevibacterium or Corynebacterium (Japanese Published Examined Patent Application No. 4015/1976) and a histidine and methionine requiring mutant of the genus Bacillus or Esterichia (Jananese Published Examined Patent Application No. 1198/1969) have been known as L-proline producing microorganisms.

SUMMARY OF THE INVENTION

We have now found excellent L-proline producing mutants belonging to the genus Brevibacterium, Corynebacterium or Microbacterium which are resistant to DL-3,4-dehydroproline.

The present invention thus provides a method for producing L-proline by fermentation which comprises culturing an L-proline producing mutant belonging to the genus Brevibacterium or Corynebacterium and resistant to DL-3,4-dehydroproline (hereinafter referred to as DP) in a culture medium, and recording the L-proline accumulated in the culture medium.

DESCRIPTION OF THE PREFERRED EMBODIMENTS

Examples of the mutants used in this invention are as follows:

Brevibacterium lactofermentum AJ 11225 (FERM-P 4370) (NRRLB-11421)

Brevibacterium flavum AJ 11226 (FERM-P 4371) (NRRLB-11422)

Corynebacterium glutamicum AJ 11227 (FERM-P 4372) (NRRLB-11423)

Microbacterium ammoniaphilum AJ 11228 (FERM-P 4373) (NRRLB-11424)

FERM-P numbers are the accession numbers of the Fermentation Research Institute, Agency of Industrial Science and Technology, Ministry of International Trade and Industry, at 2-go, 5-ban, 5-chome, Inagehigashi, Chiba-shi, Japan, and NRRL numbers are the accession numbers of the Northern Utilization Research and Development Division, U.S. Department of Agriculture, Peoria, Ill.

The mutants as mentioned above are derived from the parent strains of the genus Brevibacterium or Corynebacterium or Microbacterium which are known to produce L-proline, or wild strains of the genus Brevibacterium or Corynebacterium such as Brevibacterium lactofermentuum ATCC 13869, Brevibacterium flavum ATCC 14067, Brevibacterium divaricatum ATCC 14020, Brevibacterium roseum ATCC 13825, Corynebacterium glutamicum (Micrococcus glutamicus) ATCC 13032, Corynebacterium acetoacidophilum ATCC 13870, and Corynebacterium acetoglutamicum ATCC 15806

The growth of the parent strains are inhibited by DP, but the inhibition is suppressed by L-proline partly or completely.

The manner to induce the mutants of this invention from the parent strains is conventional such as exposing the parent strain to 2000 μg/ml N-methyl-N'-nitro-N-nitrosoguanidine at 0° C. for 20 minutes.

When the mutants of this invention have additional characteristics such as nutritional requirement or resistance to other drugs, usually they produce higher amounts of L-proline.

The experimental data of the relative growth of the mutants mentioned above in a medium containing DP are shown in Table 1 (The relative growth in a medium free from DP is shown as 100).

The relative growth shown in Table 1 is determined as follows: The microorganisms had been previously cultured for 24 hours at 30° C. on an agar slants containing 1.0 g/dl peptone, 1.0 g/dl yeast extract and 0.5 g/dl NaCl. Each one loopful inoculum of the cells on the agar slants was transferred to a culture medium of pH 7.0 containing 2.0 g/dl glucose, 1.0 g/dl ammonium sulfate 0.25 /dl urea, 0.1 g/dl $KH_2PO_4$, 0.04 g/dl $MgSO_4.7H_2O$, 1 mg/dl $FeSO_4.7H_2O$, 1 mg/dl $MnSO_4.7H_2O$, 20 μg/dl thiamine.HCl, 5 μg/dl biotin, and the amount of DP shown in Table 1.

Table 1

| Microorganisms | relative growth DP concentration | | | | |
|---|---|---|---|---|---|
| | 0 | 0.25 | 0.5 | 1.0 | 2.0 |
| Brevibacterium lactofermentum 2256 (ATCC 13869) | 100 | 47 | 32 | 15 | 10 |
| Brevibacterium lactofermentum AJ 11225 | 100 | 100 | 98 | 88 | 80 |
| Brevibacterium flavum AJ 3416 (FERM-P 1681) | 100 | 42 | 16 | 5 | 5 |
| Brevibacterium flavum AJ 11226 | 100 | 100 | 73 | 63 | 42 |
| Corynebacterium glutamicum ATCC 13032 | 100 | 53 | 28 | 15 | 11 |
| Corynebacterium glutamicum AJ 11227 | 100 | 99 | 99 | 85 | 72 |
| Microbacterium ammoniaphilum ATCC 15354 | 100 | 38 | 33 | 13 | 10 |
| Microbacterium ammoniaphilum AJ 11228 | 100 | 99 | 87 | 87 | 75 |

For the cultivation of Brevibacterium flavum AJ 3416 and AJ 11226 both of which require L-isoleucine for growth, 500 μg/ml of L-isoleucine were further contained in the culture medium. After 24 hours cultivation at 30° C. with shaking, the growth was determined by measuring the optical density of the aqueous culture medium. The results are shown in Table 1.

As a method to produce L-proline using the mutants of the present invention it is possibly to apply any known method used for the production of L-proline. The culture media are conventional media containing carbon sources, nitrogen sources, inorganic salts and, where required, other minor organic nutrients such as vitamins and amino acids. As the carbon source, carbohydrates such as beet or cane molasses and starch hydrolyzate, organic acids such as acetic acid and alcohols such as ethanol can be used. Nitrogen sources are, for example, gaseous ammonia, aqueous ammonia, ammonium salts, and urea.

Cultivation is carried out under an aerobic condition at a temperature in the range from 20° C. to 40° C. During the cultivation, the pH of the medium is preferably maintained at 6 to 9. The cultivation is continued for 20 to 100 hours.

L-proline accumulated in the resultant culture liquid can be recovered by any known methods such as by using ion-exchange resin.

Having now generally described this invention, a further understanding can be obtained by reference to certain specific examples which are provided herein for purposes of illustration only and are not intended to be limiting unless otherwise specified.

EXAMPLE 1

Twenty ml batches of a culture medium of pH 7.0, containing 10 g/dl glucose, 0.1 g/dl $KH_2PO_4$, 0.08 g/dl $MgSO_4.7H_2O$, 100 µg/dl thiamine HCl, 0.1 ml/dl soybean protein hydrolyzate, 6.0 g/dl $(NH_4)_2SO_4$, 1 mg/dl $FeSO_4.7H_2O$, 1 mg/dl $MnSO_4.4H_2O$, 450 µg/l biotin, and 5.0 g/dl $CaCO_3$ were plased in 500 ml shaking flasks, and heated for sterilization. Each batch of the medium was inoculated with *Brevibacterium lactofermentum* AJ 11225, and shaken at 30° C. for 72 hours.

L-Proline was produced in the resultant culture liquids in the amount of 22.5 g/l.

EXAMPLE 2

*Brevibacterium flavum* AJ 3416 FERM-P 1681 (L-isoleucine requiring mutant) which is not resistant to DP and *Brevibacterium flavum* AJ 11226 which is resistant to DP and which had been derived from AJ 3416 are cultured by the manner shown in Example 1 in the medium shown in Example 1 further containing 150 mg/l L-isoleucine. AJ 11226 produced 36.2 g/l L-proline, while AJ 3416 produced 32.3 g/l L-proline.

EXAMPLE 3

*Corynebacterium glutamicum* AJ 11227 was cultured by the manner shown in Example 1 and produced 12.0 g/l L-proline.

EXAMPLE 4

*Microbacterium ammoniaphilum* AJ 11228 was cultured by the manner shown in Example 1 and produced 3.3 g/l L-proline.

Having now fully described this invention, it will be apparent to one of ordinary skill in the art that many changes and modifications can be made thereto without departing from the spirit or scope of the invention set forth herein.

What is claimed as new and intended to be covered by letters patent is:

1. A method for producing L-proline by fermentation which comprises culturing an L-proline producing mutant in a culture medium until L-proline is accumulated in the culture medium, and recovering the accumulated L-proline; said mutant belonging to the genus Brevibacterium, Corynebacterium or Microbacterium and being resistant to DL-3,4-dehydroproline.

2. A method according to claim 1, wherein said mutant is selected from the group consisting of *Brevibacterium lactofermentum*, *Brevibacterium flavum*, *Corynebacterium glutamicum*, and *Microbacterium ammoniaphilum*.

3. A method according to claim 1, wherein said mutant requires L-isoleucine for growth.

4. A method for producing L-proline by fermentation which comprises culturing an L-proline producing mutant in a culture medium until L-proline is accumulated in the culture medium, and recovering the accumulated L-proline, wherein said mutant is selected from the class consisting of *Brevibacterium lactofermentum*, NRRL B-11421; *Brevibacterium flavum*, NRRL B-11422; *Corynebacterium glutamicum*, NRRL B-11423; and *Microbacterium ammoniaphilum*, NRRL B-11424, and being resistant to DL-3,4-dehydroproline.

5. A process according to claim 4, wherein the L-proline producing mutant is *Brevibacterium lactofermentum* NRRL B-11421.

6. A process according to claim 4, wherein the L-proline producing mutant is *Brevibacterium flavum* NRRL B-11422.

7. A process according to claim 4, wherein the L-proline producing mutant is *Corynebacterium glutamicum* NRRL B-11423.

8. A process according to claim 4, wherein the L-proline producing mutant is *Microbacterium ammoniaphilum* NRRL B-11424.

9. A process according to claim 4, wherein said mutant requires L-isoleucine for growth.

* * * * *